United States Patent

Dahmen et al.

[11] Patent Number: 5,712,316
[45] Date of Patent: Jan. 27, 1998

[54] POWDER-FORM CROSS-LINKED POLYMERS CAPABLE OF ABSORBING AQUEOUS LIQUIDS AND BODY FLUIDS, METHOD OF PREPARING THEM AND THEIR USE

[75] Inventors: Kurt Dahmen, Mönchengladbach; Edgar Herrmann, Nettetal; Klaus Pflüger, Krefeld, all of Germany

[73] Assignee: Chemische Fabrik Stockhausen GmbH, Krefeld, Germany

[21] Appl. No.: 569,130

[22] PCT Filed: Jun. 28, 1994

[86] PCT No.: PCT/EP94/02096

§ 371 Date: Jan. 11, 1996

§ 102(e) Date: Jan. 11, 1996

[87] PCT Pub. No.: WO95/02002

PCT Pub. Date: Jan. 19, 1995

[30] Foreign Application Priority Data

Jul. 9, 1993 [DE] Germany ............ 43 23 001.6
May 31, 1994 [DE] Germany ............ 44 18 818.8

[51] Int. Cl.$^6$ ............ C08J 9/08; C08F 20/02; C08F 8/00
[52] U.S. Cl. ............ 521/72; 521/142; 524/729; 523/105; 523/132; 523/173; 525/329.7; 525/330.2
[58] Field of Search ............ 525/329.7, 330.2; 524/729; 523/132, 173, 105; 521/72, 142

[56] References Cited

U.S. PATENT DOCUMENTS

| Re. 33,839 | 3/1992 | Chmelir et al. | 604/368 |
|---|---|---|---|
| 2,833,745 | 5/1958 | Fikentscher | 524/729 |
| 3,873,487 | 3/1975 | Minato et al. | 523/132 |
| 4,492,494 | 1/1985 | Székely et al. | 523/132 |
| 4,657,943 | 4/1987 | Wietsma | 523/132 |
| 5,118,719 | 6/1992 | Lind | 521/92 |
| 5,218,011 | 6/1993 | Freeman | 523/173 |
| 5,385,983 | 1/1995 | Graham | 525/329.7 |
| 5,409,771 | 4/1995 | Dahmen et al. | 525/329.7 |

FOREIGN PATENT DOCUMENTS 4020780  8/1991  Germany.

Primary Examiner—Tae Yoon
Attorney, Agent, or Firm—Oblon, Spivak, McClelland, Maier & Neustadt, P.C.

[57] ABSTRACT

The present invention relates to powdery, water-swellable, cross-linked polymers having a high absorption capacity for aqueous liquids, in particular body fluids, under load, which polymers are formed of:

a) 55–99.9%-wt. acid-groups-containing monomers which are neutralized to the extent of at least 50 mole-%, b) 0–40%-wt. of monomers which are copolymerizable with a), c) 0.1–5.0%-wt. of at least one cross-linking agent, d) 0–30%-wt. of a water-soluble polymer.

The cations of the salts according to a) are $Li^+$, $Na^+$, preferably $K^+$, $Cs^+$, $Rb^+$, as well as primary, secondary, and tertiary methyl ammonium ions, either alone or in combination. The polymers are manufactured in that a blowing agent based on carbon dioxide is added to the monomers, followed by polymerization, that the polymer is dried and then heated to a temperature of 100°–300° C. with one or several compounds which are reactive for surface cross-linkage. These polymers are suitable as component in sanitary articles which absorb body fluids and in wound dressings, as component in diapers, sanitary napkins, and incontinence articles, as component in current-conducting and light-transmitting cables, as soil conditioner, artificial soil for plant breeding, and as component in packaging materials.

23 Claims, No Drawings

POWDER-FORM CROSS-LINKED POLYMERS CAPABLE OF ABSORBING AQUEOUS LIQUIDS AND BODY FLUIDS, METHOD OF PREPARING THEM AND THEIR USE

The present invention relates to powdery, cross-linked polymers absorbing aqueous liquids and blood (superabsorbers) and having improved properties with regard to absorption velocity, swelling and retention capacity for aqueous liquids under high load. The present invention further relates to a process for the manufacture of said polymers and to their use in absorbent sanitary articles, such as diapers, in the adult incontinence, feminine hygiene, and for wound dressing.

Superabsorbers are water-insoluble, cross-linked polymers which, under swelling and formation of hydrogels, are capable of absorbing large amounts of aqueous liquids and body fluids, such as urine or blood, and of retaining the absorbed liquid amount under a certain pressure or load. Owing to said characteristic absorption properties the polymers are mainly used for incorporating them in sanitary articles, for example, diapers and sanitary napkins.

Initially, only the very high swelling capacity on contact with liquids, also referred to as free swelling capacity, had been the main factor in the development of superabsorbers; later it turned out, however, that not only the amount of absorbed liquid is of importance but also the stability of the swollen gel. However, absorbency, also referred to as swellability or free swelling capacity, on the one hand, and gel strength of a cross-linked polymer, on the other hand, represent contrary properties, as is known from U.S. Re No. 32,649. This means that polymers having a particularly high absorbency exhibit a poor strength of the swollen gel so that the gel is deformable under pressure (e.g., the load of a body) and further liquid distribution and absorption is prevented. According to U.S. Re 32,649 a balanced relation between absorption capacity (gel volume) and gel strength is to be aimed at so as to ensure liquid absorption, liquid transport, dryness of the diaper and the skin when such superabsorbers are used in a diaper structure. In this connection, not only the polymer's capability of retaining a liquid under subsequent pressure, after swelling freely first, is of importance but also the fact that liquids are absorbed even against a simultaneously acting pressure, i.e. during the liquid absorption; this is the case in practice when a baby or person sits or lies on a sanitary article or when shear forces are acting, e.g., by movements of legs. In EP No. 0 339 461 this particular absorption property is referred to as absorption under load.

The only way to meet the increasing trend of reducing the size and thickness of sanitary articles for esthetic and environmental reasons (reduction of waste in the land fill) is to reduce the large-volume fluff pulp portion in diapers and to increase the portion of superabsorber at the same time. For that reason the superabsorber has to take over additional functions with respect to liquid absorption and transport thereof, which were previously performed by the fluff pulp and which cannot be accomplished by the known superabsorbers to a satisfactory extent.

This particularly applies to cases where the proportion of superabsorber in the absorbent zone of a sanitary article is increased to 40 to 60%-wt. and more. Owing to the poor absorption rate of the superabsorber in case of several mictions, so-called "leakage" may result caused by a blockade in the liquid transport and liquid distribution, in particular under pressure, i.e., the liquid is no longer absorbed by the sanitary article, thus resulting in a wet diaper surface and, consequently, wet skin.

To provide superabsorbent polymers having the characteristic properties, such as high absorption capacity, high gel strength and high absorbency under load, it is necessary to subject the polymer resins to a subsequent surface treatment.

For example, U.S. Pat. No. 4,043,952 recommends polyvalent metal compounds to improve the dispersibility in water, and U.S. Pat. No. 4,051,086 proposes the use of glyoxal to improve the absorption rate. DE-OS 27 40 169 describes the production of absorbents based on potassium and ammonium acrylate-containing polymers which are treated with polyols and are used in diapers and other sanitary and medical articles in the form of powders and sheets. The secondary treatment of resins using cross-linking agents comprising bi- or polyfunctional groups capable of reacting with the carboxyl or carboxylate groups or other groups contained in the polymer is described in EP 0 083 022 (to improve the dispersibility in water and the absorbency), DE-OS 33 31 644 (to improve the resistance to salt solutions at high water absorption rates), DE-OS 35 07 775 (to increase the salt resistance with good liquid absorption and gel strength), DE-OS 35 23 617 (to improve flowability and prevent agglomeration), DE-OS 36 28 482 (to improve water absorption when used repeatedly), and EP 0 349 240 (to achieve a balance between absorbency and absorption rate as well as gel strength and suction force). In these cases, the powder is either directly mixed with the components, optionally with using small amounts of water and solvent, or dispersed in an inert solvent, or polymers comprising 10 to 40%-wt. of water are dispersed in a hydrophilic or hydrophobic solvent and mixed with the cross-linking agent, either subsequently or simultaneously. Suitable cross-linking agents include polyglycidyl ethers, halo epoxy compounds, polyols, polyamines, or polyisocyanates. Additionally, polyfunctional aziridine compounds, alkyl-di-(tri)-halogenides, and oil-soluble polyepoxy compounds are mentioned in DE-OS 33 14 019, EP 0 317 106, and DE-OS 37 37 196. In DE-OS 35 03 458 (to obtain a polymer having good water absorption capacity, high water absorption rate and high gel strength in a non-tacky gel) the application of a cross-linking agent on a polymeric resin is effected in the presence of an inert inorganic powdery material, such as $SiO_2$, without using organic solvents. According to DE-PS 40 20 780, an improved absorption under load is achieved by cross-linking the surface of a polymer resin with 0.1 to 5%-wt. of alkylene carbonate.

All these processes have in common that a temperature treatment of the resins is carried out subsequently.

The superabsorbers obtained according to the prior art have a high swellability under a load of 20 $g/cm^2$, which, according to the teaching of DE-PS 40 20 780, amounts to 28 to 34 g/g for 0.9% solution of sodium chloride under this load (AUL). Additionally, it is reported that the products manufactured according to this patent have a high initial rate of liquid absorption under load so that 80% of the total capacity are achieved after only 15 minutes.

It turned out, however, that the relatively high absorption rate of the polymer resins obtainable by a secondary treatment according to the state of the art particulary exists if the liquid absorption takes place under a simultaneously acting load. However, in case of swelling without load the absorption must still be improved.

For the practical use of absorbent resins in sanitary articles a rapid liquid absorption under load-free swelling is very important since diapers for babies and pads for adults, for example, are not always subjected to a load by body weight, and in these cases a rapid absorption of large liquid amounts must also take place in order to prevent leakage.

Additionally, the absorbent resins known from the art have the disadvantage that the swelling capacity substantially decreases under a load of more than 20 g/cm$^2$. Accordingly, in a known polymer having an AUL of 30 g/g under a load of 20 g/cm$^2$ the AUL decreases to 15 g/g under a load of 40 g/cm$^2$ and to 9 g/g at 60 g/cm$^2$. This reduction in the absorption capacity under high pressure has a particularly negative effect in new diaper structures with increased superabsorber proportions, in which the absorber resin has to ensure the liquid transport to remote storing regions. In this case, owing to insufficient gel stability, a soft gel forms which deforms under a high pressure and that impairs further liquid transport due to the so-called "gel-blocking".

Accordingly, it is the object of the present invention to provide superabsorbent polymers which, in addition to an improved absorption velocity and a high retention capacity, have a particularly high absorption under an increased load.

This object is achieved by a powdery, water-swellable, cross-linked polymer absorbing water, aqueous liquids, in particular body fluids, which polymer is formed of a) 55–99.9%-wt. of polymerized unsaturated, polymerizable, acid-groups-comprising monomers, said monomers being present as salts neutralized to the extent of at least 50 mole-%, b) 0–40%-wt. of polymerized unsaturated monomers which are copolymerizable with a), c) 0.1–5.0%-wt. of a cross-linking-agent, d) 0–30%-wt. of a water-soluble polymer, with the sum of a)–d) amounting to 100%-wt, and which polymer has an absorption capacity for a 0.9% NaCl-solution of at least 12 g/g polymer, preferably 16 g/g polymer at a load of 60 g/cm$^2$.

Most surprisingly it turned out that superabsorbent polymers having neutralized acid groups whose cations are selected from the group consisting of lithium, sodium, and preferably potassium, rubidium, cesium, ammonium, monomethyl ammonium, dimethyl ammonium, or trimethyl ammonium have a considerably improved absorption velocity if in the production of the polymer products, prior to the polymerization step, a blowing agent based on carbon dioxide has been added to the monomer solution. At the same time, the superabsorbers according to the invention have an improved absorption under a high load owing to the fact that the particulate absorbent resins have been treated with a reactive multifunctional secondary cross-linking agent and have then been heated to 120°–300° C.

U.S. Pat. No. 4,529,739 describes absorbents which, starting from hydrophobic polymers in the form of latex, are manufactured by saponification under the addition of carbonates as blowing agents.

It is known from U.S. Pat. No. 5,118,719 to produce superabsorbent polymers having improved rate of water absorption by means of carbonate-containing blowing agents which, by releasing carbon dioxide, result in a hydrogel having a microcellular structure. As can be seen in the examples of U.S. Pat. No. 5,118,719, the absorption rate is improved, however, the absorption capacity reduced. Absorbent resins manufactured according to U.S. Pat. No. 5,118,719 have a considerably poorer absorption under load (AUL) than the products known from the art, e.g., those according to DE-PS 40 20 780. By the known prior art processes no water-absorbing resins are obtained which exhibit an improvement in the absorption rate in case of swelling without load, although they have a high absorption under a load of 20 g/cm$^2$. Thus, the aforementioned prior art does not contain any reference as to a way of how the property combinations of improved absorption rate in both unloaded and loaded absorption and improved absorption capacity under a high pressure can be achieved.

It was found that improved water-absorbing resins are obtained if hydrogels having a microcellular structure, which are produced by using blowing agents, are used and these resins are subjected to a treatment of surface cross-linking, e.g., according to the process of DE-PS 40 20 780. Additionally, it was found that the cations of lithium, sodium, and, preferably, of potassium, rubidium, cesium, as well as of ammonium, monomethyl ammonium, dimethyl ammonium or trimethyl ammonium, which are present in the salts resulting from the neutralization of the acid-group-containing monomers, have a decisive influence on absorption capacity and rate. It turned out that a considerable improvement in the absorption capacity under load and an improvement in the absorption rate occurred.

Preferred cations are the potassium ion and the ammonium ion.

Water-absorbing resins which may be used for the surface-cross-linking treatment are obtained by polymerizing 55–99.9%-wt. of monomers having acid groups, e.g., acrylic acid, methacrylic acid, 2-acrylamido-2-methylpropane sulfonic acid, or mixtures of these monomers; the acid groups are present in neutralized form to the extent of at least 50 mole percent. Particularly preferred is a resin formed of cross-linked acrylic acid or methacrylic acid which is neutralized to the extent of 50 to 80 mole percent.

Neutralization of the acid groups in the aqueous monomer solutions is effected with bases according to known methods, e.g., with lyes, carbonates or amines. Besides caustic soda solution, preferred neutralizing agents are, above all, potash lye and ammonia. Further monomers suitable for the production of the water-absorbing resins include 0–40%-wt. of acrylamide, methacrylamide, hydroxyethyl acrylate, dimethylaminoalkyl(meth)-acrylate, dimethyl-aminopropyl acrylamide, or acrylamidopropyl trimethyl ammonium chloride. Proportions exceeding 40% of these monomers will deteriorate the swell capacity of the resins.

As cross-linking agent any compound may be used which has at least two ethylenically unsaturated double-bonds or one ethylenically unsaturated double-bond and one functional group reactive with acid groups, or several functional groups reactive with acid groups. Examples thereof include: acrylates and methacrylates of polyols, such as butanediol diacrylate, hexanediol dimethacrylate, polyglycol diacrylate, trimethylolpropane triacrylate, or allyl acrylate, diallyl acrylamide, triallyl amine, diallyl ether, methylene bisacrylamide, or N-methylol acrylamide, further polyglycidyl ethers, such as ethylene glycol diglycidyl ethers and glycerol polyglycidyl ethers and/or polyols, such as glycerol, trimethylolpropane and/or polyalkylene glycols, such as polyethylene glycol 200 to 600. Polyamines can also be used.

0 to 30%-wt. partially or completely saponified polyvinyl alcohol, polyvinyl pyrrolidone, starch or starch derivatives, polyglycols, or polyacrylic acids may be comprised as water-soluble polymers in the water-absorbing resin. The molecular weight of said polymers is not critical provided that they are water-soluble. Preferred water-soluble polymers are starch or polyvinyl alcohol or mixtures of these polymers. The preferred content of said water-soluble polymers in the water-absorbing resin amounts to about 1–5%- wt., in particular if starch and/or polyvinyl alcohol are present as soluble polymers. The water-soluble polymers may be present as graft polymers having the acid-group-containing polymers.

In addition to resins obtained by cross-linking polymerization of partially neutralized acrylic acid, those are preferably used which additionally comprise portions of graft-polymerized starch or of polyvinyl alcohol.

The production of the absorbent resins of the present invention is carried out according to known methods. It may either be effected by the aqueous solvent polymerization (gel process) or by the inverse emulsion/suspension polymerization.

According to the present invention, a blowing agent based on carbon dioxide as a carbonate or in the form of carbon dioxide, either gaseous or solid, must be dissolved or dispersed in the monomer solution or dispersion. A quantity of 0.1–5.0%-wt., relative to anhydrous polymer substance, e.g., of sodium carbonate, sodium hydrogencarbonate, potassium carbonate, potassium hydrogen-carbonate, ammonium carbonate, magnesium carbonate, calcium carbonate, or mixtures of these substances may be used as carbonates. If solid carbon dioxide (dry ice) is used, cooling of the monomer solution or dispersion to temperatures between −10° C. and 30° C., preferably between 0° and 10° C., and removal of oxygen may simultaneously be effected.

With respect to the surface-cross-linking treatment there are no specific limitations as to the particle shape of the absorber-resin used. The polymer may be present in the form of small beads obtained by inverse suspension polymerization, or in the form of irregularly shaped particles originating from drying and pulverizing the mass obtained by solvent polymerization. Drying of the hydrogel is effected at temperatures of 80°–200° C., in particular at 100°–180° C., and preferably at 120°–150° C. Usually, the particle size is between 20 and 3,000 μm, preferably between 50 and 1,000 μm.

For the surface-cross-linking treatment, the water-absorbing resins may be mixed with the known secondary cross-linking agents based on at least bifunctional compounds which are reactive with acid groups, in particular carboxyl groups. The water-absorbing resins may be mixed with the secondary cross-linking agents either directly, in a solution of water and alcohol or in a solution of water. The quantity of the secondary cross-linking agent amounts to 0.01 to 10%-wt., preferably 0.01 to 4.0%-wt., and most preferably 0.01 to 2.0%-wt., relative to the water-absorbing resin. Mixtures of different secondary cross-linking agents may also be used. The amount of alcohol is determined by the solubility of the agent and is kept as low as possible for technical reasons, e.g., protection against explosions. Suitable alcohols are methanol, ethanol, butanol, or butyl glycol as well as mixtures of said alcohols. The preferred solvent is water which is used in an amount of 0.3–5.0%-wt., relative to resin. It is also possible to apply the secondary cross-linking agent from a powder mixture, e.g., using an inorganic carrier material, such as $SiO_2$.

Preferred surface-cross-linking, at least bifunctional compounds which are reactive with acid groups include polyols, such as glycerol and/or polyalkylene glycols, such as polyethylene glycol and/or polyamines, such as triethanolamine. Alkylene carbonates according to DE-PS 40 20 780 are particularly preferred for the use as surface cross-linking agents.

To achieve the desired properties, the agent has to be distributed evenly on the resin powder. For this purpose, mixing is effected in suitable mixers, e.g., fluidized bed mixers, paddle mixers, milling rolls, or twin-worm-mixers.

It is also possible to carry out the treatment of the absorbent resin during one of the process steps in the production of the polymeric resin. To this end, a particularly suitable process is the inverse suspension polymerization. The thermal treatment which follows the addition of the surface cross-linking agent is carried out at 100°–300° C., preferably at 120°–250° C. The temperature depends on the residence time and the kind of reactant. At a temperature of 150° C. the thermal treatment must be carried out for several hours, whereas at 250° C. a few minutes, e.g., 0.5 to 5 minutes, are sufficient to obtain the desired properties. The thermal treatment may be carried out in conventional dryers or ovens; examples thereof include rotary kilns, fluidized bed dryers, paddle dryers, disk dryers, or infrared dryers.

The polymers according to the present invention may be manufactured on the large scale by continuous or discontinuous processes. The agents according to the present invention may be used for a variety of applications. If they are used, for example, as absorbing material in sanitary napkins and diapers, or for wound dressing purposes, they have the property to absorb rapidly large quantities of menstrual blood, urine or other body fluids. The absorbency and absorption velocity is absolutely superior to that of the known products. Since the agents of the invention absorb and retain the absorbed fluids under a high pressure load, they are particularly easy to use. They are particularly suitable for the use in concentrations that—relative to hydrophilic fiber material, e.g., fluff pulp—are higher than those possible to date. In application, the proportion of the absorbing polymer may exceed 35%-wt.; it may amount to 15–100%-wt. and preferably 30–70%-wt., relative to the quantity formed by the absorbent polymer and the fluff. The polymers of the present invention stand out for an improved distribution of the fluid, in particular in the layers substantially containing polymer, immediately after liquid absorption.

Additionally, the polymers according to the present invention used as absorbents for water and aqueous liquids are useful in current-conducting and light-transmitting cables, in packaging materials and as soil improvers and artificial soil for plant breeding.

Test Methods

To characterize the water-absorbing resins, retention (TB), absorption under load (AUL) and absorption velocity/rate (AV and Vortex) were measured.

The retention is determined according to the tea bag method and reported as average value of three measurements. Approximately 200 mg of resin are enclosed in a tea bag and immersed in 0.9% NaCl-solution for 20 minutes. Then the tea bag is centrifuged in a centrifuge (diameter: 23 cm; rpm: 1,400) for 5 minutes and weighed. One tea bag without water-absorbing resin is used as blank.

$$\text{Retention} = \frac{\text{Weight} - \text{Blank reading}}{\text{Initial weight}} \; [g/g].$$

The absorption under load (AUL) is determined according to the method described in EP 0 339 461, page 7: The initial weight of superabsorber is placed in a cylinder provided with sieve bottom, the powder is loaded by a piston exerting a pressure of 20 $g/cm^2$, 40 $g/cm^2$ and 60 $g/cm^2$. The cylinder is subsequently placed on a Demand-Absorbency-Tester (DAT), and the superabsorber is allowed to suck 0.9% NaCl-solution for one hour.

The absorption velocity (AV) is determined according to a modified form of the method Absorption under load (AUL), as described in EP 0 339 461, page 7. In this case, the absorption of the 0.9% solution of sodium chloride is measured without loading the powder with additional weights. After 15 s, 30 s, 1, 3, 5, 10 and 15 min. the absorbed quantity of liquid is determined by weighing. The measurement is carried out as triple determination.

The Vortex Test to determine the absorption rate is carried out following the method described in WO 87/03208 on page 9. The initial weight amounts to 2.0 g polymer; the time starting from sprinkling the polymer into the liquid until disappearance of the vortex is measured in seconds.

EXAMPLES

Comparative Example 1

According to example 4 of DE-PS 40 20 780, an aqueous monomer solution consisting of a mixture of sodium acrylate and acrylic acid, at a mole ratio of 70:30, and triallylamine as cross-linking agent is polymerized. The resultant gel is comminuted, dried, ground and screened out to a particle size ranging from 90–850 μm.

The powdery product is mixed with a mixture of 0.2/0.1/2.0% 1,3-dioxolan-2-one/water/ethanol, relative to powder, and heated to 180° C. for 1 hour. The product properties are shown in Table 1.

Comparative Example 2

According to example 4 of U.S. Pat. No. 5,118,719, an aqueous monomer solution consisting of a mixture of sodium acrylate and acrylic acid, at a mole ratio of 70:30, and triallyl amine as cross-linking agent is polymerized after addition of 0.5% basic magnesium carbonate. The resultant gel is comminuted, dried, ground, and screened out (90–850 μm). The product properties are shown in Table 1.

Example 1

Comparative Example 1 is repeated. However, prior to polymerization, 0.5% basic magnesium carbonate as $CO_2$-releasing blowing agent is added to the monomer solution, as described in U.S. Pat. No. 5,118,719. The resultant powdery polymer is subjected to the same secondary treatment as in Comparative Example 1.

TABLE 1

| Comparative Example | 1  | 2      |
|---|---|---|
| TB                  | 30 | 26 g/g |
| AUL                 |    |        |
| 20 g/cm²            | 30 | 20 g/g |
| 40 g/cm²            | 15 | 9 g/g  |
| 60 g/cm²            | 9  | 8 g/g  |
| Vortex              | 83 | 18 s   |
| AV                  |    |        |
| 15 s                | 2  | 7 g/g  |
| 30 s                | 4  | 15 g/g |
| 1 min               | 9  | 24 g/g |
| 3 min               | 19 | 33 g/g |
| 5 min               | 25 | 36 g/g |
| 10 min              | 34 | 37 g/g |
| 15 min              | 39 | 37 g/g |

TB = Tea bag test
AUL = Absorption under load
AV = Absorption velocity

Examples 2–8

An aqueous monomer solution consisting of a mixture of

Example 2: potassium acrylate
Example 3: potassium acrylate
Example 4: potassium acrylate
Example 5: potassium acrylate
Example 6: ammonium acrylate
Example 7: methyl ammonium acrylate
Example 8: cesium acrylate and acrylic acid at a mole ratio of 70/30 and triallyl amine as cross-linking agent was polymerized under addition of a carbonate and 0–1% polyvinyl alcohol (PVA). The resultant gel was comminuted, dried, ground and screened out to 90–850 μm.

The powdery, screened polymer was mixed with a mixture of 1,3-dioxolan-2-one or ethylene glycol diglycidyl ether (EGDE), water and ethanol and heated to 120°–300° C. for 0.5–1 hour.

Examples 9 and 10

An aqueous monomer solution consisting of a mixture of

Example 9: potassium acrylate
Example 10: ammonium acrylate and acrylic acid, at a mole ratio of 70/30, and triallylamine as cross-linking agent with the addition of 0–1% polyvinyl alcohol (PVA) was saturated with carbon dioxide (by introducing dry ice) and then polymerized. The resultant gel was comminuted, dried, ground and screened out to 90–850 μm. The powdery, screened polymer was mixed with a mixture of 1,3-dioxolan-2-one and ethylene glycol diglycidyl ether (EGDE), water and ethanol and heated to 120°–300° C. for 0.5–1 hour. Composition, reaction conditions, and product properties are listed in Table 2.

TABLE 2

| Example | 2 | 3 | 4 | 5 |
|---|---|---|---|---|
| Cation | K | K | K | K |
| Cross-linker [%] | 0.4 | 0.4 | 0.4 | 0.5 |
| Carbonate [%] | 1.5 potass | 2.5 potass. | 1.5 potass. | 0.5 potass. |
| PVA [%] | 1.0 | 1.0 | — | 1.0 |
| 1,3-dioxolan-2-one [%] | 0.5 | 0.5 | 0.5 | 0.5 |
| Water [%] | 2.0 | 2.0 | 2.0 | 2.0 |
| Ethanol [%] | 4.0 | 2.0 | 2.0 | 2.0 |
| Time [min] | 30 | 30 | 30 | 30 |
| Temperature [C.] | 200 | 180 | 200 | 200 |
| TB | 27 | 28 | 27 | 27 g/g |
| AUL | | | | |
| 20 g/cm² | 25 | 28 | 27 | 25 g/g |
| 40 g/cm² | 20 | 20 | 22 | 23 g/g |
| 60 g/cm² | 18 | 14 | 18 | 21 g/g |
| Vortex | 21 | 16 | 21 | 23 s |
| AV | | | | |
| 15 s | 12 | 10 | 10 | 9 g/g |
| 30 s | 19 | 20 | 16 | 16 g/g |
| 1 min | 26 | 28 | 24 | 23 g/g |
| 3 min | 36 | 38 | 31 | 33 g/g |
| 5 min | 38 | 43 | 33 | 35 g/g |
| 10 min | 39 | 44 | 35 | 36 g/g |
| 15 | 40 | 45 | 37 | 38 g/g |

| Example | 6 | 7 | 9 | 10 |
|---|---|---|---|---|
| Cation | $NH_4$ | $NH_3CH_3$ | K | $NH_4$ |
| Cross-linker [%] | 0.3 | 0.3 | 0.3 | 0.3 |
| Carbonate | 1.5 $NH_4^+$ | 1.5 $NH_4^+$ | $CO_2$ | $CO_2$ |
| Saturation temp. °C. | — | — | 4 | 13 |
| Polyvinyl alcohol | — | — | 1.0 | 1.0 |
| EGDE | 0.25 | — | — | 0.25 |

TABLE 2-continued

| | | | | |
|---|---|---|---|---|
| 1,3-dioxolan-2-one | — | 1.0 | 0.5 | — |
| Water | 2.0 | 8.0 | 2.0 | 2.0 |
| Ethanol | 2.0 | 8.0 | 2.0 | 2.0 |
| Time [min] | 60 | 60 | 30 | 60 |
| Temperature [°C.] | 120 | 140 | 200 | 120 |
| TB | 33 | 35 | 27 | 33 g/g |
| AUL | | | | |
| 20 g/cm$^2$ | 28 | 24 | 25 | 29 g/g |
| 40 g/cm$^2$ | 22 | 17 | 20 | 23 g/g |
| 60 g/cm$^2$ | 18 | 12 | 16 | 17 g/g |
| Vortex | 27 | 28 | 15 | 12 s |
| AV | | | | |
| 15 s | 8 | 6 | 12 | 14 g/g |
| 30 s | 13 | 12 | 17 | 20 g/g |
| 1 min | 19 | 18 | 28 | 27 g/g |
| 3 min | 31 | 26 | 36 | 36 g/g |
| 5 min | 34 | 29 | 40 | 41 g/g |
| 10 min | 40 | 34 | 43 | 44 g/g |
| 15 | 42 | 37 | 44 | 45 g/g |

Comparative Example 3

Comparative Example 2 is repeated. The caustic soda solution required for neutralization is replaced by potash lye at the same mole ratio. Prior to polymerization, 1.5% potassium carbonate is added to the monomer solution.

Comparative Example 4

Comparative Example 1 is repeated. The caustic soda solution required for neutralization is replaced by potash lye at the same mole ratio. The powdery polymer thus obtained is subjected to the same secondary treatment as in Comparative Example 1.

Comparative Example 5

Comparative Example 3 is repeated. The potash lye required for neutralization is replaced by ammonia water at the same mole ratio. Prior to polymerization, 0.5% ammonium carbonate is added to the monomer solution.

Comparative Example 6

Comparative Example 4 is repeated. The potash lye required for the partial neutralization is replaced by ammonia water at the same mole ratio. The powdery product is mixed with a mixture consisting of 0.25/2.0/2.0 EGDE/water/acetone, relative to powder, and heated to 120° C. for 1 hour.

| Comparative Ex. | 3 | 4 | 5 | 6 |
|---|---|---|---|---|
| TB | 31 | 30 | 57 | 54 g/g |
| AUL | | | | |
| 20 g/cm$^2$ | 10 | 24 | 8 | 9 g/g |
| 40 g/cm$^2$ | 9 | 16 | 7 | 8 g/g |
| 60 g/cm$^2$ | 7 | 11 | 6 | 8 g/g |
| Vortex | 70 | 24 | 12 | 20 s |
| AV | | | | |
| 15 s | 3 | 8 | 2 | 8 g/g |
| 30 s | 7 | 14 | 3 | 12 g/g |
| 1 min | 13 | 22 | 3 | 17 g/g |
| 3 min | 22 | 32 | 5 | 22 g/g |
| 5 min | 29 | 38 | 7 | 29 g/g |

-continued

| Comparative Ex. | 3 | 4 | 5 | 6 |
|---|---|---|---|---|
| 10 min | 34 | 40 | 9 | 31 g/g |
| 15 min | 36 | 42 | 10 | 34 g/g |

Comparative Example 7

Prior to the secondary treatment, the polymer of Example 2 is screened out to the fraction 100–300 μm and is not subjected to a secondary treatment. The swell rate (swelling height after 1 min) and the swelling height after 10 min. were determined according to the so-called FIRET-Test, a method of Messrs. Lantor B.V.; Veenendaal/NL (cf. table). The test was modified such that instead of the tape 0.2 g superabsorber was evenly distributed on the bottom of the measuring pot and covered with a nonwoven or tissue (simulated tape).

Example 11

Prior to the secondary treatment, the polymer of Example 2 is screened out to the fraction 100–300 μm and then subjected to the same secondary treatment as in Example 1. Testing of the product properties is carried out as in Comparative Example 7 (cf. table).

Example 12

After the secondary treatment, the polymer of Example 2 is screened out to the fraction 100–300 μm. Testing of the product properties is carried out as in Comparative Example 7 (cf. table).

| Comparative | Example 7 | Example 11 | Example 12 |
|---|---|---|---|
| Swell rate | 2.2 | 8.2 | 9.1 mm/min |
| Swell. height after 10 min. | 11.8 | 12 | 12 mm |

The products according to the present invention obtained in Examples 11 and 12 are particularly suitable as component in current-conducting and light-transmitting cables as sealing against penetrating water.

We claim:

1. A powdery, water-swellable, cross-linked polymer having a microcellular structure obtainable by polymerizing a composition comprising
   a) 55–99.9%-wt. of unsaturated, polymerizable acid-groups-containing monomers, said monomers being present as salts neutralized to the extent of at least 50 mole-%,
   b) 0–40%-wt. of unsaturated monomers which are copolymerizable with a),
   c) 0.1–5.0%-wt. of at least one cross-linking agent,
   d) 0–30%-wt. of a water-soluble polymer, with the sum of a)–d) amounting to 100%-wt,
   and e) 0.1–5.0%-wt., relative to the sum of a)–d), of a blowing agent based on carbon dioxide, drying the polymer, adding one or more secondary surface-cross-linking agents for surface cross-linking, and heating to a temperature of 100°–300° C.

2. The polymer according to claim 1, wherein the polymer has an absorption capacity for a 0.9% NaCl-solution of at least 10 g/g polymer within 30 seconds.

3. The polymer according to claim 1, wherein the polymer has a particle size of 20 to 3,000 μm.

4. The polymer according to claim 1 wherein the acid-group-containing monomers a)

are selected from the group consisting of acrylic acid, methacrylic acid, acrytamidomethylpropane sulfonic acid, and mixtures of these monomers, the monomers b)

are selected from the group consisting of acrylamide, methacrylamide, hydroxyalkyl acrylate, dimethylaminoalkyl(meth)-acrylate, dimethylaminopropyl(meth) acrylamide, the quaternary amine and ammonium salts of these monomers, and of mixtures of these monomers, the cross-linking agent c)

is selected from the group consisting of alkylene bisacrylamide, N-methylol acrylamide, butanediol diacrylate, hexanediol dimethacrylate, polyglycol diacrylate, trimethylolpropane triacrylate, allyl acrylate, diallyl acrylamide, triallyl amine, diallyl ether, polyglycidyl ethers, polyols, trimethylolpropane, polyalkylene glycols, and polyamines, and mixtures of these cross-linking agents, and the blowing agent based on carbon dioxide is a carbonate selected from the group consisting of $Na_2CO_3$, $K_2CO_3$, $(NH_4)_2CO_3$, $MgCO_3$, $CaCO_3$, $NaHCO_3$, $K_2CO_3$, mixtures of these carbonates, and carbon dioxide in gaseous or solid form.

5. A process for the production of the polymers according to claim 1 comprising polymerizing the monomers a), the monomers b) which are copolymerizable with a), and the cross-linking agent c) in the presence of water-soluble polymer d), and the blowing agent based on carbon dioxide under addition of radical forming initiators or by initiation by exposure to light or irradiation under formation of hydrogel; drying the polymer; adding one or more secondary surface cross-linking agents for surface cross-linking to the polymer; and heating to a temperature of 100°–300° C.

6. The process according to claim 5 wherein the polymer is dried at temperatures of 80° to 200° C.

7. The process according to claim 5 wherein the polymer is ground after drying.

8. The process according to claim 6 wherein the polymer is screened out to a particle size of 20–3,000 μm.

9. The process according to claim 5 wherein heating to a temperature of 100° to 300° C. is effected for surface cross-linkage.

10. The process according to claim 5 wherein the polymerization is effected in aqueous solution.

11. The process according to claim 5 wherein the polymerization is effected in a water-in-oil dispersion.

12. An article which absorbs a fluid, comprising the polymer of claim 4.

13. The article of claim 12, wherein said article is a diaper, sanitary napkin, a wound dressing, a packaging material, artificial soil, or incontinence article.

14. The article of claim 13, wherein said article is a diaper containing fluff and, wherein the diaper contains 15–100% by weight of said polymer, relative to the weight of said polymer and fluff.

15. The article of claim 14, containing 35–100% by weight of said polymer.

16. The article of claim 15, containing 30–70% by weight of said polymer.

17. A current-conducting or light-transmitting cable containing the polymer of claim 1.

18. Conditioned soil comprising soil and the polymer of claim 1.

19. The polymer according to claim 1, wherein the salts according to a) are of one or more cations selected from the group consisting of sodium, lithium, potassium, ammonium, methylammonium and cesium.

20. The polymer according to claim 1, wherein the polymer has an absorption capacity for a 0.9% NaCl-solution of at least 12 g/g polymer at a load of 60 g/cm².

21. The polymer according to claim 1, wherein the polymer has an absorption capacity for a 0.9% NaCl-solution of at least 16 g/g polymer at a load of 60 g/cm².

22. The polymer according to claim 1, wherein the polymer has an absorption capacity for a 0.9% NaCl-solution of at least 16 g/g polymer within 30 seconds.

23. The polymer according to claim 1, wherein the polymer has a particle size of 100 to 1,000 μm.

* * * * *